United States Patent [19]
Jautelat et al.

[11] 4,425,282
[45] * Jan. 10, 1984

[54] PREPARATION OF 3-(ARYLVINYL)-2,2-DIMETHYL-CYCLOPROPANE-1-CARBOXYLIC ACID ESTERS AND NEW INTERMEDIATE THEREFOR

[75] Inventors: Manfred Jautelat, Burscheid; Dieter Arlt, Cologne; Reinhard Lantzsch, Leverkusen; Rainer Fuchs, Wuppertal; Hans-Jochem Riebel, Wuppertal; Rolf Schröder, Wuppertal; Horst Harnisch, Much, all of Fed. Rep. of Germany

[73] Assignee: Bayer Aktiengesellschaft, Leverkusen, Fed. Rep. of Germany

[ * ] Notice: The portion of the term of this patent subsequent to Apr. 20, 1999 has been disclaimed.

[21] Appl. No.: 138,043

[22] Filed: Apr. 7, 1980

[30] Foreign Application Priority Data

Apr. 23, 1979 [DE] Fed. Rep. of Germany ....... 2916417

[51] Int. Cl.³ ..................... C07C 121/60; C07C 51/58
[52] U.S. Cl. ........................ 260/465 D; 260/544 D; 560/8; 560/9; 560/10; 560/19; 560/55; 560/56
[58] Field of Search ..................... 260/544 D, 465 D; 560/8, 9, 10, 19, 55, 56

[56] References Cited

U.S. PATENT DOCUMENTS

| 4,161,535 | 7/1979 | Meyer et al. | 260/544 D |
| 4,204,071 | 5/1980 | Anderson et al. | 260/544 D |
| 4,229,368 | 10/1980 | Anderson et al. | 560/8 |
| 4,325,873 | 4/1982 | Jautelat et al. | 260/465 D |

FOREIGN PATENT DOCUMENTS

| 2539895 | 3/1976 | Fed. Rep. of Germany . |
| 2706184 | 8/1977 | Fed. Rep. of Germany . |
| 2738150 | 3/1978 | Fed. Rep. of Germany . |
| 2750182 | 5/1978 | Fed. Rep. of Germany . |
| 2827101 | 6/1978 | Fed. Rep. of Germany . |
| 2800073 | 7/1978 | Fed. Rep. of Germany . |
| 2740849 | 3/1979 | Fed. Rep. of Germany . |

OTHER PUBLICATIONS

Chem Abstracts 48:657d.
Chem. Abstracts 87 (Subject Index) p. 2684CS.
Chem. Abstracts ('62–'66 Subject Index), p. 11,000S.
Roedig et al., Chem. Ber. 111, 860–868 (1978).
Kondo et al., Tetrahedron Letters, No. 48, pp. 4359–4362, (1976).
Chem. Abstracts 87:5478t.
Chem. Abstracts 87:102011t.

Primary Examiner—Ethel G. Love
Attorney, Agent, or Firm—Sprung, Horn, Kramer & Woods

[57] ABSTRACT

A process for the preparation of a 3-(arylvinyl)-2,2-dimethyl-cyclopropane-1-carboxylic acid ester of the formula

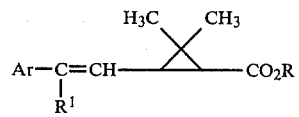

in which
Ar is an aromatic radical,
R is alkyl or an alcohol radical customary in pyrethroids, and
R¹ is hydrogen, fluorine or chlorine,
comprising reacting a compound of the formula

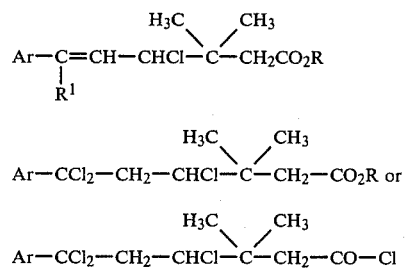

with respectively, one, two or three equivalents of a base at a temperature between about −20° and +60° C. The compounds are insecticidally active. Numerous syntheses of the starting materials, some involving new intermediates, are also shown.

4 Claims, No Drawings

PREPARATION OF 3-(ARYLVINYL)-2,2-DIMETHYL-CYCLOPROPANE-1-CARBOXYLIC ACID ESTERS AND NEW INTERMEDIATE THEREFOR

The present invention relates to an unobvious process for the preparation of certain 3-(arylvinyl)-2,2-dimethylcyclopropane-1-carboxylic acid esters, and to new intermediate products for carrying out this process and their preparation.

It has already been disclosed that certain esters of 3-styryl-2,2-dimethylcyclopropanecarboxylic acids have insecticidal properties (German Offenlegungsschrift No. 2,738,150). They are prepared by effecting linkage of the C-C double bond of the styryl group by a Wittig reaction, in which butyllithium is used as the base and which must be carried out at −78° C. under an inert gas. This synthesis route is not practicable for an industrial preparation.

Furthermore, the 2,2-dimethyl-3-formyl-1-carboxylic acid ester used as the starting material for this reaction is available only with difficulty on an industrial scale.

1. The present invention now provides a process for the preparation of a 3-(2-arylvinyl)-2,2-dimethyl-cyclopropane-1-carboxylic acid ester of the general formula

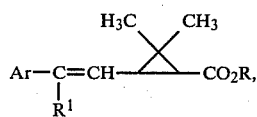

in which
Ar represents a substituted or unsubstituted, carbocyclic or heterocyclic, aromatic radical,
$R^1$ represents a hydrogen, fluorine or chlorine and
R represents alkyl or an alcohol radical customary in pyrethroids,
in which (a) a compound of the general formula

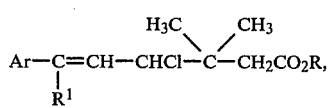

or (b) a compound of the general formula

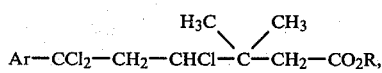

or (c) a compound of the general formula

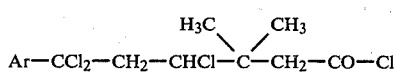

in which formulae Ar, $R^1$ and R have the meanings indicated above, is reacted with, respectively, one, two or three equivalents of a base, if appropriate in the presence of a diluent, between −20° and +60° C.

2. It has also been found that the compounds of the formula (I) are preferably obtained when the reaction is carried out below 50° C.

3. The new compounds of the general formula (II) in which

Ar, $R^1$ and R have the meanings indicated above, have also been found.

4. The new compounds of the general formula (III) in which

Ar and R have the meanings indicated under 1 above, have also been found

5. The new compounds of the general formula (IV) in which

Ar has the meaning indicated above, have also been found.

6. A process has also been found for the preparation of a compound of the general formula (II), which is characterized in that (a) hydrogen chloride is split off from a compound of the general formula (III) by the action of heat, or (b) a compound of the general formula (IV) is reacted with an alcohol of the general formula

in which R has the meaning indicated under 1 above,
or (c) a compound of the general formula

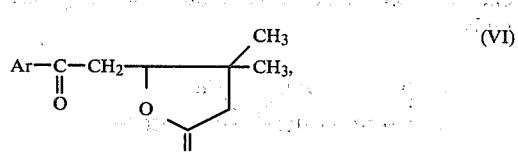

in which Ar has the meaning indicated above, is reacted with at least two equivalents of phosphorus pentachloride, and the resulting reaction solution is then reacted with an alcohol of the formula

in which R has the meaning indicated under 1 above,
or (d) a compound of the general formula

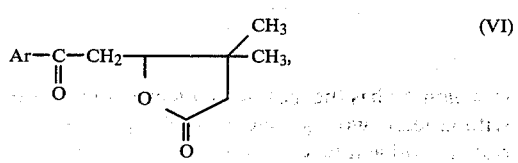

in which Ar has the meaning indicated above, is reduced, water is split off and the product is reacted with a chlorinating agent in the presence of an alcohol of the general formula

in which R has the meaning indicated under 1 above, or, successively, the lactone ring is first opened with a chlorinating agent and the product is then reacted with the alcohol,
or (e) a compound of the general formula

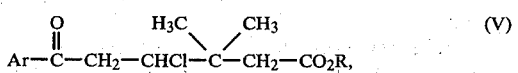

in which Ar and R have the meanings indicated under 1 above, is reacted with sulphur tetrafluoride, or (f) a compound of the general formula $$Ar-CCl_2-CH_2-CHCl-\underset{\underset{CH_3}{|}}{\overset{\overset{CH_3}{|}}{C}}-CH_2-CO_2R, \quad (III)$$

in which Ar and R have the meanings indicated above, or a compound of the general formula $$Ar-CCl_2-CH_2-CHCl-\underset{\underset{CH_3}{|}}{\overset{\overset{CH_3}{|}}{C}}-CH_2-CO-Cl, \quad (IV)$$

in which Ar has the meaning indicated above, is reacted with anhydrous hydrogen fluoride and, if appropriate, the product is then reacted with an alcohol of the general formula $$R-OH \quad (XIII),$$

in which R has the meaning indicated under 1 above.

7. A process has also been found for the preparation of a compound of the general formula (III), which is characterized in that a compound of the general formula $$Ar-\overset{\overset{O}{\|}}{C}-CH_2-CHCl-\underset{\underset{CH_3}{|}}{\overset{\overset{CH_3}{|}}{C}}-CH_2-CO_2-R, \quad (V)$$

in which Ar and R have the meanings indicated under 1 above, is reacted with phosphorus pentachloride in a diluent below 30° C.

8. A process has also been found for the preparation of a compound of the general formula (IV), characterized in that a compound of the general formula (VI)

in which Ar has the meaning indicated above, is reacted with at least two equivalents of phosphorus pentachloride in a diluent below 30° C.

9. The new compounds of the formula (V) in which Ar and R have the meanings indicated under 1 above, have also been found.

10. A process has also been found for the preparation of a compound of the general formula (V), characterized in that a compound of the general formula (VI) is reacted with a chlorinating agent in the presence of an alcohol of the formula $$R-OH \quad (XIII),$$

in which R has the meaning indicated under 1 above, or, successively, the lactone ring is opened with a chlorinating agent and the product is then reacted with the alcohol.

11. The new compounds of the general formula (VI) in which Ar has the meaning indicated above, have also been found.

12. A process has also been found for the preparation of a compound of the general formula (VI), characterized in that a compound of the general formula $$CH_2=CH-\underset{\underset{CH_3}{|}}{\overset{\overset{CH_3}{|}}{C}}-CH_2CO_2R, \quad (VII)$$

in which R denotes $C_1$-$C_4$-alkyl,
is reacted with a compound of the general formula $$Ar-CO-Hal \quad (VIII),$$

in which
  Ar has the meaning indicated under 1 above and
  Hal denotes halogen, preferably chlorine,
in the presence of a Friedel-Crafts catalyst.

13. It has also been found that a compound of the general formula (VI), which can be summarized under the general formula (IX)

in which
  X represents hydrogen, $C_{1-4}$-alkyl, halogen, aryl, aralkyl, aryloxy, arylthio, $C_{1-4}$-alkoxy, or $C_{1-4}$-alkylthio,
  Y represents hydrogen or is identical to X, or
  X and Y represent methylenedioxy or ethylenedioxy, and
  Z represents O, S or —CH=CH—,
is obtained by a process in which a compound of the general formula (X)

wherein X, Y and Z have the meanings indicated above, is reacted with the acid chloride of the formula (XI)

in the presence of a Friedel-Crafts catalyst and, if appropriate, in the presence of a diluent.

14. The new compound of the formula (XI) has also been found.

15. A process has also been found for the preparation of the compound of the formula (XI), which is characterized in that the compound of the formula

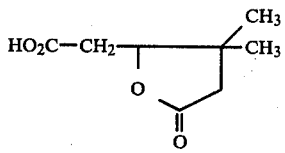

(XII)

is reacted with a chlorinating agent.

The preparative processes according to the invention, using the new intermediate products according to the invention, are used for the preparation, inter alia, of compounds known from DE-OS (German Published Specification) No. 2,738,150. They are simpler and, on an industrial scale, easier to carry out than the process known from DE-OS (German Published Specification) No. 2,738,150 for the preparation of these compounds.

If 6-(4'-chloro)-phenyl-4,6-dichloro-3,3-dimethylhex-5-enoic acid ethyl ester is used as the starting substance in process variant 1(a), the course of the reaction can be illustrated by the following equation.

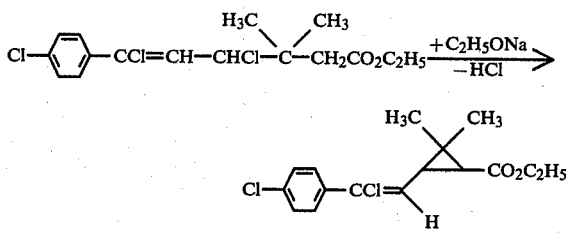

The general formula (II) provides a definition of the starting substances which can be used in process variant 1(a). Preferably, in this formula, Ar represents a phenyl, naphthyl, furane, thiophene or pyridine radical which is optionally substituted by one or more identical or different substituents X, X represents halogen, cyano, nitro, aryl, aralkyl, aryloxy, arylthio, $C_{1-4}$-alkyl, $C_{1-4}$-alkoxy, $C_{1-4}$-alkylthio, $C_{1-2}$-halogenoalkyl, $C_{1-4}$-halogenoalkoxy, $C_{1-4}$-halogenoalkylthio, optionally halogen-substituted $C_{1-4}$-alkylsulphonyl, dialkylamino with 1 or 2 carbon atoms in each alkyl substituent or optionally halogen-substituted methylenedioxy or ethylenedioxy, and $R^1$ represents hydrogen, fluorine or chlorine.

Particularly preferably,

Ar represents a phenyl ring which is substituted by one or two identical or different substituents X, X represents hydrogen, fluorine, chlorine, bromine, cyano, nitro, methyl, ethyl, isopropyl, tert.-butyl, methoxy, ethoxy, methylmercapto, trifluoromethyl, methylsulphonyl, trifluoromethylsulphonyl, dimethylamino, diethylamino or optionally halogen-substituted methylenedioxy or ethylenedioxy, R represents $C_{1-4}$-alkyl or a 3-phenoxybenzyl radical which is optionally substituted by halogen or cyano and $R^1$ represents hydrogen, fluorine or chlorine.

Very particularly preferably,

Ar represents a phenyl ring which is substituted in the 3-position and/or 4-position by on or two identical or different substituents X, X represents hydrogen, fluorine, chlorine, bromine, methyl, methoxy, ethoxy, trifluoromethyl, nitro, methylenedioxy or ethylenedioxy, R represents methyl or ethyl and $R^1$ represents chlorine.

The compounds of the formula (II) have not before been described in the literature; their preparation is described below.

If 6-(4'-fluorophenyl)-4,6,6-trichloro-3,3-dimethylhexanoic acid methyl ester is used as the starting substance in process variant 1(b), the course of the reaction can be represented by the following equation:

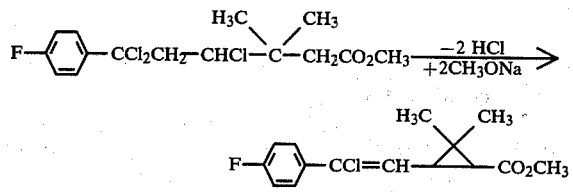

The general formula (III) provides a definition of the starting substances which can be used in process 1(b). The preferred and particularly preferred substituents Ar and R are the same as in the case of process variant 1(a). The compounds of the formula (III) have not before been described in the literature; their preparation is described below.

If 6-(4'-methyl)-phenyl-4,6,6-trichloro-3,3-dimethylhexanoic acid chloride is used as the starting substance in process variant 1(c), the course of the reaction can be represented by the following equation:

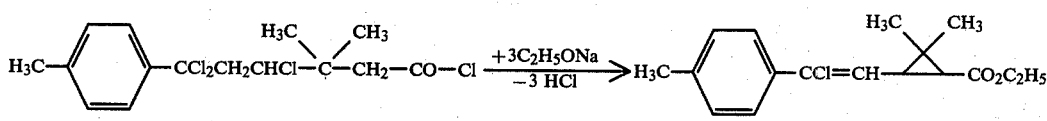

The general formula (IV) provides a definition of the starting substances which can be used in process variant 1(c). The preferred and particularly preferred substituent Ar is the same as in the case of process variant 1(a). The compounds of the formula (IV) have not hitherto been disclosed in the literature; their preparation is described below.

Process variants 1(a), (b) and (c) are carried out by reacting the starting substances (II), (III) and (IV) with respectively 1, 2 or 3 equivalents of a base, if appropriate in the presence of a diluent.

An alcoholate, such as sodium methylate, potassium ethylate, sodium ethylate, sodium isopropylate, sodium tert.-butylate or potassium tert.-butylate, is preferably used as the base.

The alcohol corresponding to the base is preferably employed as the diluent, but other inert diluents, for example hydrocarbons, such as toluene, xylene or cyclohexane, chlorinated hydrocarbons, such as chlorobenzene, or ethers, such as diisopropyl ether, tetrahydrofuran or dioxane can also be employed additionally or exclusively.

The process is carried out at temperatures between $-20°$ C. and $+60°$ C., preferably between $20°$ C. and $50°$ C.

A similar reaction is described in DE-OS (German Published Specification) No. 2,539,896. However, while the preferred temperature range in this reaction is between 60° and 100° C., when sodium methylate or sodium ethylate is used (page 31), only very little product of the formula (I) is obtained under these conditions, and, predominantly, a further mol of hydrogen halide is split off, a triple bond being formed.

Surprisingly, it has been found that this is avoided if the reaction is carried out below 60° C.

Another advantage of the process according to the invention is that only one of the 4 possible stereoisomers is very preferentially formed. It has the trans-configuration with respect to the cyclopropane ring.

The insecticidal and acaricidal esters of these isomers have a particularly good activity.

The following cyclopropanecarboxylic acid esters of the formula (I) are preferably prepared by process 1: 2,2-Dimethyl-3-[2'-chloro-2'-(4'-fluoro-phenyl)-vinyl]-cyclopropane-1-carboxylic acid methyl and ethyl ester, 2,2-dimethyl-3-[2'-chloro-2'-(4'-chloro-phenyl)-vinyl]-cyclopropane-1-carboxylic acid methyl and ethyl ester, 2,2-dimethyl-3-[2'-chloro-2'-(4'-bromo-phenyl)-vinyl]-cyclopropane-1-carboxylic acid methyl ester and ethyl ester, 2,2-dimethyl-3-[2'-chloro-2'-phenyl-vinyl]-cyclopropane-1-carboxylic acid methyl ester and ethyl ester, 2,2-dimethyl-3-[2'-chloro-2'-(3'-chloro-phenyl)-vinyl]-cyclopropane-1-carboxylic acid methyl ester and ethyl ester, 2,2-dimethyl-3-[2'-(phenyl)-vinyl]-cyclopropane-1-carboxylic acid methyl ester and ethyl ester, 2,2-dimethyl-3-[2'-(4'-chloro-phenyl)-vinyl]-cyclopropane-1-carboxylic acid methyl ester and ethyl ester, 2,2-dimethyl-3-[2'-chloro-2'-(3',4'-dichloro)-phenyl-vinyl]-cyclopropane-1-carboxylic acid methyl ester and ethyl ester, 2,2-dimethyl-3-[2'-chloro-2'-(4'-methyl-phenyl)-vinyl]-cyclopropane-1-carboxylic acid methyl ester and ethyl ester, 2,2-dimethyl-3-[2'-chloro-2'-(3'-methyl-phenyl)-vinyl]-cyclopropane-1-carboxylic acid methyl ester and ethyl ester and 2,2-dimethyl-3-[2'-chloro-2'-(3'-methyl-4'-chloro-phenyl)-vinyl]cyclopropane-1-carboxylic acid methyl ester and ethyl ester.

As already stated, the compounds of the general formula (II) are new. They are obtained by the process indicated under 6 above, by (a) splitting off hydrogen chloride from compounds of the general formula (III) by the action of heat, or (b) reacting compounds of the formula (IV) with alcohols, or (c) reacting compounds of the formula (VI) with phosphorus pentachloride and then reacting the products with an alcohol, or (d) reducing compounds of the formula (VI), splitting off water from the products and reacting the compounds obtained with a chlorinating agent in the presence of an alcohol, or, successively, first opening the lactone ring with a chlorinating agent and then reacting the product with an alcohol, or (e) reacting compounds of the formula (V) with sulphur tetrafluoride, or (f) reacting compounds of the formula (III) or (IV) with anhydrous hydrofluoric acid and then, if appropriate, reacting the products with an alcohol.

If 6-(4'-chloro)-phenyl-4,6,6-trichloro-3,3-dimethylhexanoic acid ethyl ester is used as the starting substance in process 6(a), the course of the reaction can be represented by the following equation:

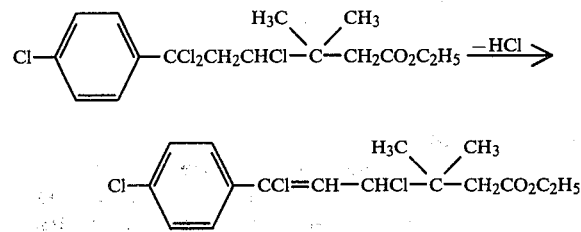

The general formula (III) provides a definition of the starting substances which can be used in process 6(a). The preferred and particularly preferred substituents Ar and R are the same as those in the case of process variant 1(a).

As stated above, the compounds of the formula (III) are new; their preparation is described below.

Process 6(a) is carried out by warming the starting substances of the formula (III), if appropriate in a diluent, to a temperature between 25° and 80° C., preferably to a temperature between 30° and 50° C. During this procedure, hydrogen chloride is split off. Possible diluents are, in particular, hydrocarbons, such as benzene, toluene, xylene, benzine, cyclohexane or petroleum ether; chlorinated hydrocarbons, such as methylene chloride, chloroform, carbon tetrachloride, dichloroethane or chlorobenzene; and nitriles, such as acetonitrile.

If appropriate, isolation of the compounds of the general formula (III) can be dispensed with, so that process 6(a) follows on from process 7 (below) immediately.

If 6-(4'-methoxy)-phenyl-4,6,6-trichloro-3,3-dimethylhexanoic acid chloride is used as the starting substance in process 6(b), the course of the reaction can be represented by the following equation:

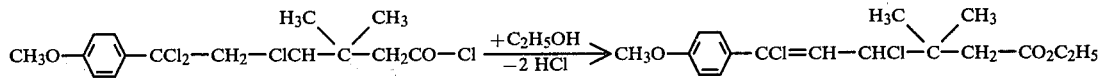

The general formula (IV) provides a definition of the starting substances which can be used in process 6 (b). The preferred and particularly preferred substituents Ar are the same as those in the case of process variant 1(a). As stated above, the compounds of the formula (IV) are new; their preparation is described below.

Process 6(b) is carried out by adding the starting substance of the formula (IV), if appropriate in a diluent, to an alcohol of the general formula R—OH, the preferred meaning of the R being the same as that in the case of process variant 1(a), at a temperature between −20° and 80° C., preferably between 0° C. and 30° C. In order to bring the reaction to completion, the mixture is then stirred at elevated temperature, preferably between 30° and 60° C., for a further period. Excess alcohol or any of the solvents which can also be used in process 6(a) can be used as the diluent.

If 3,3-dimethyl-4-(4'-chloro)-phenacyl-γ-butyrolactone and ethanol are used as starting substances in process 6(c) the course of the reaction can be represented by the following equation:

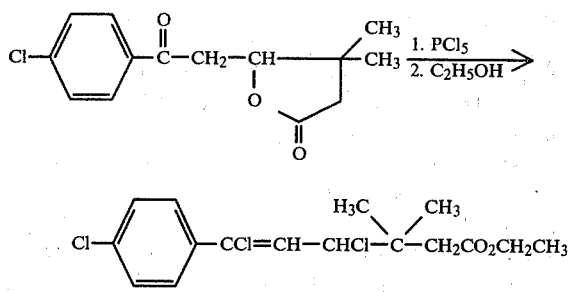

The general formula (VI) provides a definition of the starting substances which can be used in process 6(c) and in process 6(d). The preferred and particularly preferred substituents Ar are the same as those in the case of process variant 1(a). As stated above, the compounds of the formula (VI) are new; their preparation is described below.

Phosphorus pentachloride can be used as the chlorinating agent.

Process 6(c) is carried out by initially introducing the starting substance of the general formula (VI) and reacting it with at least two equivalents of the chlorinating agent. A slight excess is favorable.

In contrast to the generally customary procedure (Houben-Weyl, Volume V,3, page 912 et seq.) for the reaction of ketones with phosphorus pentachloride, the process is preferably carried out in the presence of a diluent. Possible diluents are the same as those mentioned for process 6(a).

Surprisingly, by using a diluent and metering in the phosphorus pentachloride, the side reactions which are otherwise customary, for example chlorination in the α-position relative to the carbonyl group or addition of hydrogen chloride onto the chlorovinyl group, can be avoided.

The reaction temperature is between −20° and +60° C., preferably between 0° C. and 35° C.

The subsequent esterification is effected by adding excess alcohol R—OH dropwise, analogously to process 6(b).

The mixture is worked up by washing until neutral, separating off the organic phase and distilling off the solvent and the phosphoric acid ester. At this stage, purification by distillation can usually be dispensed with.

If 3,3-dimethyl-4-phenacyl-α-butyrolactone is used as the starting substance in process 6(d), the course of the reaction can be represented by the following equation:

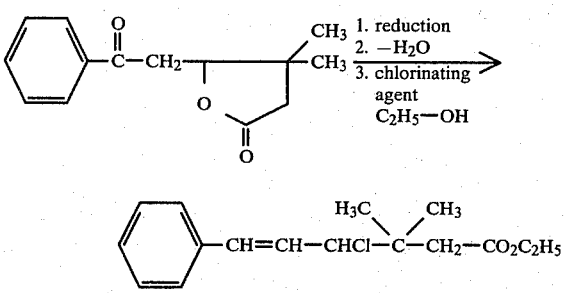

In principle, possible reducing agents for use in process 6(d) are any of the agents by which a ketone is reduced to the alcohol without the lactone ring being attacked. Examples which may be mentioned are: complex borohydrides, such as sodium borohydride, or hydrogen in the presence of, for example, nickel catalysts, palladium catalysts or platinum catalysts, such as, for example, Raney nickel. Sodium borohydride is preferred.

Process 6(d) is carried out by a procedure in which, after the reducing step, which is carried out in a manner which is in itself customary, the products are dehydrated, that is to say water is split off.

An acid catalyst is preferably employed for the dehydration. Examples which may be mentioned are: oxalic acid, sulphuric acid, phosphoric acid, potassium bisulphate, p-toluenesulphonic acid, aluminum oxide and silicates. The alcohol formed can also be acetylated and acetic acid can then be split off by heating. Acetylation is effected with acetyl chloride or acetic anhydride. The third step of process 6(d) corresponds to process 10 (below).

If 6-(4'-chloro)-phenyl-6-oxo-4-chloro-3,3-dimethyl-hexanoic acid ethyl ester is used as the starting substance in process 6(e), the course of the reaction can be represented by the following equation:

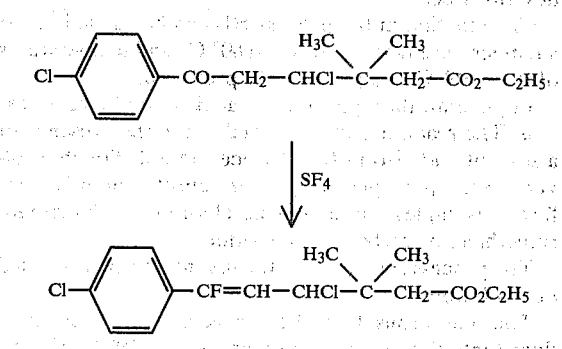

The formula (V) provides a definition of the starting substances which can be used in process 6(e). The preferred and particularly preferred substituents Ar and R are the same as those in the case of process variant 1(a). The compounds of the formula (V) are new; their preparation is described below.

Process 6(e) is carried out by a procedure in which the starting substance of the formula (V), is heated, together with sulphur tetrafluoride, to a temperature between 100° and 180° C., preferably to 120°-150° C., in an autoclave. If appropriate, HF, BF$_3$, TiF$_4$ or similar compounds can be used as catalysts. The mixture is worked up in the customary manner; the crude product may be further reacted directly according to process variant 1(a).

If 6-phenyl-4,6,6-trichloro-3,3-dimethyl-hexanoic acid ethyl ester is used as the starting substance in process 6(f), the course of the reaction can be represented by the following equation:

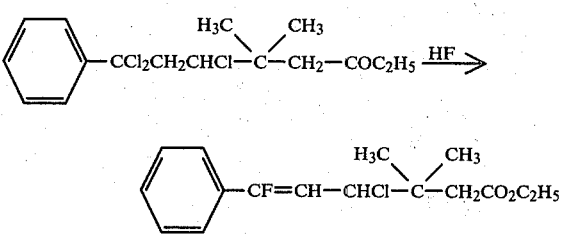

If 6-phenyl-4,6,6-trichloro-3,3-dimethyl-hexanoic acid chloride is used as the starting substance in process 6(f), the course of the reaction can be represented by the following equation:

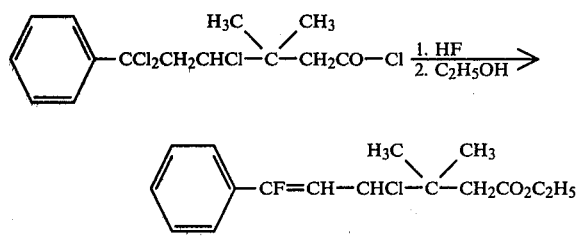

The general formulae (III) and (IV) provide definitions of the starting substances which can be used in process 6(f).

The preferred and particularly preferred substituents Ar and R are the same as those in the case of process variant 1(a). As stated above, the compounds of the formula (III) and (IV) are new; their preparation is described below.

The reaction in the process 6(f) can be carried out at a temperature from −20° C. to 80° C., and temperatures of 0° to 50° C. are particularly preferred.

In general, the hydrofluoric acid is employed in excess. The reaction can be carried out in the presence of a solvent and also in the absence thereof. Possible solvents are, quite generally, inert aprotic liquids. Preferred examples are methylene chloride, trichlorofluoromethane or carbon tetrachloride.

The process according to the invention can be carried out as follows:

The anhydrous hydrofluoric acid is initially introduced into the reaction vessel at about −20° C. and the starting substance of the formula (III) or (IV), dissolved in methylene chloride, is added dropwise, while stirring. Hydrogen chloride is already evolved vigorously at 0° C. When the evolution of hydrogen chloride has ended, the temperature can be increased to room temperature or above. The excess hydrofluoric acid and the solvent are then distilled off, under normal pressure or reduced pressure. If a starting substance of the formula (IV) has been used, the residue is reacted with an alcohol of the formula R—OH to give the ester and the product may then be employed directly in process 1(a).

If 6-(3'-chloro)-phenyl-6-oxo-4-chloro-3,3-dimethyl-hexanoic acid ethyl ester is used as the starting substance in process 7, the course of the reaction can be represented by the following equation:

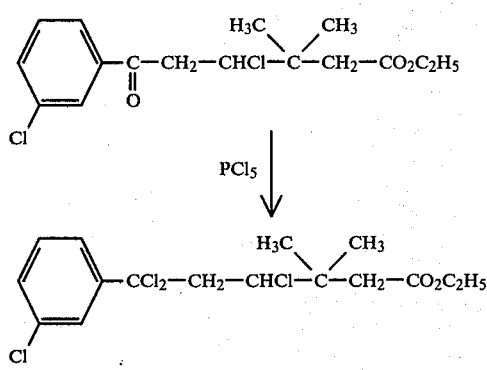

The general formula (V) provides a definition of the starting substances which can be used in process 7. The preferred and particularly preferred substituents Ar and R are the same as those in the case of process variant 1(a). The compounds of the formula (V) are new; their preparation is described below.

It has been found that the compounds (III) are obtained from the compounds of the formula (V) only if the reaction is carried out in a diluent below 30° C.

Process 7 is carried out by a procedure in which the starting substances of the general formula (III) are dissolved in a diluent. Possible diluents are the same as those mentioned for process 6(a); petroleum ether, cyclohexane, toluene and chlorobenzene are preferred.

The reaction temperature is between −20° C. and 30° C., preferably between 0° and 25° C.

The mixture is worked up by adding ice-water, washing the organic phase until neutral and distilling off the solvent.

The structure is proved by a nuclear magnetic resonance spectrum.

If 3,3-dimethyl-4-(4'-bromo)-phenacyl-γ-butyrolactone is used as the starting substance in process 8, the course of the reaction can be represented by the following equation:

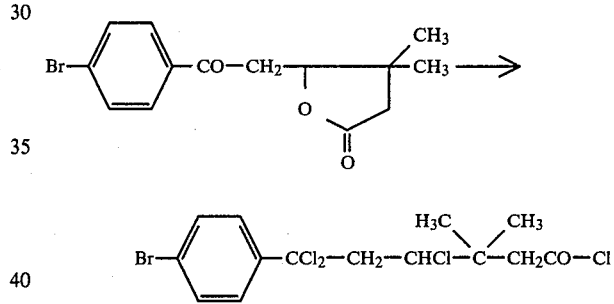

The general formula (VI) provides a definition of the starting substances which can be used in process 8. The preferred substituents are the same as those in the case of process variant 1(a). The compounds of the formula (VI) are new; their preparation is described below.

It has also been found that the compounds (IV) are obtained from the compounds (VI) only if the reaction is carried out in a diluent below 30° C.

Process 8 is carried out by a procedure in which the starting substances of the general formula (VI) are dissolved in a diluent.

Possible diluents are the same as those mentioned for process 6(a); petroleum ether, cyclohexane, toluene and chlorobenzene are preferred.

The reaction temperature is between −20° and +30° C., preferably between 0° and 25° C.

The compounds of the formula (IV) can be isolated by gently distilling off the solvent and phosphorus oxychloride, or they can be further reacted directly according to process variant 1(c) or process 6(b).

If 3,3-dimethyl-4-(4'-fluoro)-phenacyl-γ-butyrolactone and ethanol are used as starting substances in process 10, the course of the reaction can be represented by the following equation:

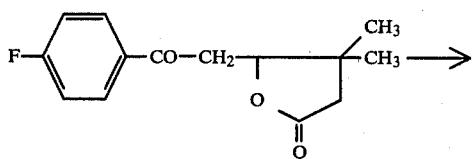

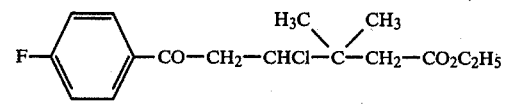

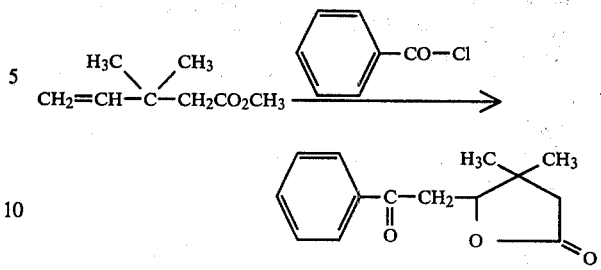

The general formula (VI) provides a definition of the starting substances which can be used in process 10. The preferred and particularly preferred substituents Ar are the same as those in the case of process variant 1(a). The compounds of the formula (VI) are new; their preparation is described below.

The second starting substance for process 10 is an alcohol of the formula R—OH, the preferred meaning of R being the same as that in the case of process variant 1(a).

The following chlorinating agents can be used in process 10; hydrogen chloride, thionyl chloride, phosgene or phosphorous trichloride, and hydrogen chloride and thionyl chloride are preferred; if appropriate, dimethylformamide is used as a catalyst.

Lactone ring openings of this type are in principle known, but in no case do such lactones contain an additional carbonyl group. Conditions had therefore to be found which resulted in only the desired reaction proceeding, and not, for example, (1) acid-catalyzed self-condensation reactions of the ketone (acetophenone, for example, reacts with itself in this manner under catalysis by hydrogen chloride) or (2) chlorination of the carbonyl group or of the hydrogen atoms in the α-position relative to the carbonyl group.

Process 10 is carried out by a procedure in which the starting substance of the formula (VI) is dissolved in an alcohol of the formula R—OH, if appropriate a diluent is also added, and the chlorinating agent is then passed in or added dropwise. An exothermic reaction starts; in order to avoid the above-mentioned side-reactions, the temperature should in no case exceed 80° C., and the reaction is preferably carried out between 20° and 50° C.

Possible diluents are, in particular, benzene, toluene, benzine, petroleum ether, cyclohexane, chlorobenzene or xylene.

In principle, it is also possible first to open the lactone ring and then to add the alcohol. In this case, the starting compound (VI), if appropriate in one of the diluents mentioned, is heated to a temperature between 50° and 80° C. (higher temperatures are not appropriate) with addition of a chlorinating agent, if necessary under pressure. The alcohol R—OH is then added dropwise or pumped in.

The compounds of the formula (V) are isolated by gently distilling off the solvent. Further purification is difficult, but also unnecessary. The crude compound of the formula (V) can be used directly for process 7.

If 3,3-dimethyl-pent-4-enoic acid methyl ester and benzoyl chloride are used as starting substances in process 12, the course of the reaction can be represented by the following equation:

The general formulae (VII) and (VIII) provide definitions of the starting substances which can be used in process 12. The preferred and particularly preferred substituents Ar are the same as those in the case of process variant 1(a). The compounds of the formula (VII) (DT-OS (German Published Specification) No. 2,539,895) and (VIII) are known.

Examples of compounds of the formula (VIII) are: benzoyl chloride, 4-chlorobenzoyl chloride, 3-chlorobenzoyl chloride, 2-chlorobenzoyl chloride, 4-fluorobenzoyl chloride, 4-bromobenzoyl chloride, 3,4-dichlorobenzoyl chloride, 4-methyl-benzoyl chloride, 4-phenoxy-benzoyl chloride, 3-phenoxy-benzoyl chloride, 4-trifluoromethyl-benzoyl chloride, 3-trifluoromethylbenzoyl chloride, 3-trifluoromethyl-4-chlorobenzoyl chloride, pentachlorobenzoyl chloride, pentafluorobenzoyl chloride, 2,4,6-trifluoro-3,5-dichlorobenzoyl chloride, 2,6-difluoro-3,5-dichloro-benzoyl chloride, thiophene-2-carboxylic acid chloride, 4-bromo-thiophene-2-carboxylic acid chloride, furane-2-carboxylic acid chloride, pyridine-3-carboxylic acid chloride, pyridine-4-carboxylic acid chloride, 4-nitrobenzoyl chloride, 4-methyl-sulphonylbenzoyl chloride, naphthalene-1-carboxylic acid chloride, naphthalene-2-carboxylic acid chloride, 4-methoxy-benzoyl chloride and 3,4-dimethoxybenzoyl chloride.

Possible catalysts are in principle any of the customary Friedel-Crafts catalysts. The particularly preferred catalyst is tin tetrachloride or, if appropriate, mixtures with aluminum chloride, titanium tetrachloride, zinc chloride or iron(III) chloride. Using aluminum chloride by itself, the compounds formed are not those of the formula (VI) but those of the formula (V). The Friedel-Crafts catalyst is employed in an equimolar amount or in an amount which is less or more than the equimolar amount. Process 12 can be carried out with or without a diluent. If a diluent is used, possible diluents are, for example, methylene chloride, chloroform, dichloroethane, tetrachloroethane, nitromethane or nitrobenzene.

The process according to the invention is carried out by a procedure in which the Friedel-Crafts catalyst is initially introduced, if appropriate in a diluent, and the acid halide of the general formula (VIII) is added, while cooling. An ester of the general formula (VII) is then added dropwise at a temperature between −25° C. and +50° C., preferably at a temperature between 0° C. and 25° C.

It is, however, also possible to initially introduce an acid halide of the formula (VIII) together with an ester of the formula (VII), if appropriate in the presence of a diluent, and then to meter in the Friedel-Crafts catalyst.

To accelerate the reaction, when mixing of the reactants has ended, the reaction can be carried out at elevated temperature, for example at 25° to 150° C., preferably at 30° to 100° C. The end of the reaction can be recognized by the end of the evolution of gas. The mixture is worked up, after being rendered acid, in the customary manner by extraction. The crude product of the general formula (VI) can be purified by recrystallization.

The course of the reaction is extremely surprising, since lactone formation under such mild conditions was not known hitherto.

If toluene and 3,3-dimethyl-4-chlorocarbonylmethyl-γ-butyrolactone are used as starting substances in process 13, which is for the preparation of compounds of the general formula

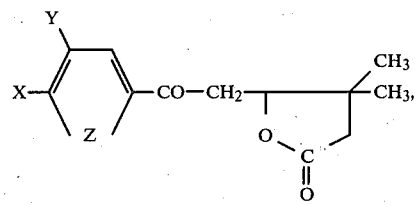
(IX)

the course of the reaction can be represented by the following equation:

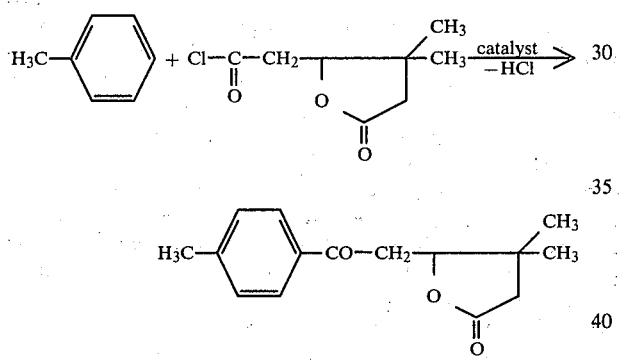

The formulae (X) and (XI) provide definitions of the starting substances which can be used in process 13. The compound (XI) has not been described hitherto in the literature; its preparation is described below.

The compounds of the formula (X) are known, and examples which may be mentioned are: benzene, fluorobenzene, chlorobenzene, bromobenzene, toluene, ethylbenzene, diphenyl ether, xylene and o-dichlorobenzene. Possible catalysts are in principle any of the customary Friedel-Crafts catalysts, such as aluminum chloride, tin tetrachloride, titanium tetrachloride, hydrogen fluoride, boron trifluoride, iron(III) chloride, zinc chloride, polyphosphoric acids, perfluoroalkanesulphonic acids (if appropriate in polymeric form) and, if appropriate, mixtures thereof.

The process is preferably carried out in the presence of a diluent. Possible diluents are: methylene chloride, chloroform, dichloroethane, tetrachloroethane, nitrobenzene and nitromethane. Methylene chloride is preferred.

The reaction according to process 13 is extremely surprising, since it had to be expected that the lactone ring would also react, in the following manner:

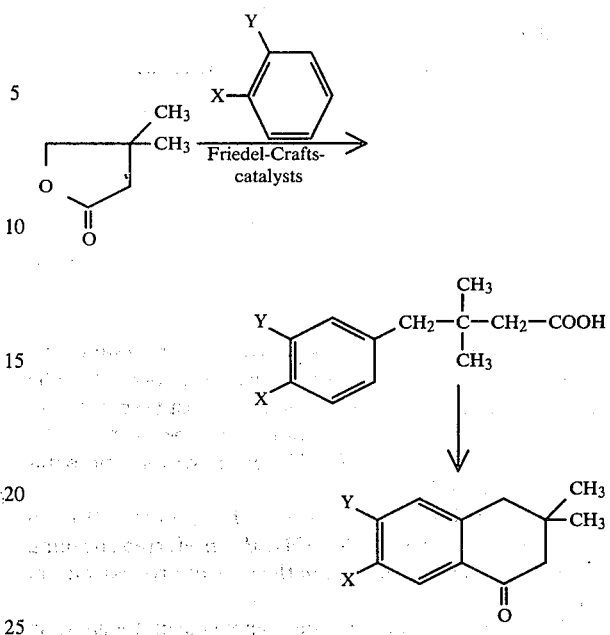

and in addition cyclization to give the tetralone would have been expected. Ring openings of 5-membered lactone rings with aromatics by a Friedel-Crafts reaction in the manner formulated above are known and take place under very mild conditions (Houben-Weyl; Volume VI, 2, page 812 et seq.).

That such a reaction of the lactone with the aromatics of the formula (X) does not take place, is also surprising, especially since the Friedel-Crafts catalyst must be employed in at least an equimolar amount, and even better in excess.

Process 13 is preferably carried out as follows:

The acid chloride (XI) is initially introduced in a diluent, and the Friedel-Crafts catalyst is added at a temperature between <10° C. and +5° C. The aromatic compound, if appropriate also dissolved in a diluent, is then added dropwise. If very active Friedel-Crafts catalysts are used (for example aluminum chloride or tin tetrachloride), this addition is effected at −10° to +5° C. and in the case of Friedel-Crafts catalysts of lower activity (for example zinc chloride, iron chloride, titanium tetrachloride or perfluoroalkanesulphonic acids), the aromatic compound is added dropwise at room temperature. The mixture is then subsequently stirred at room temperature; in the case of less active catalysts, the reaction must be carried out at elevated temperature if necessary.

If an aromatic compound which is slow to react, for example chlorobenzene, is used, it is advisable not to accelerate the reaction by increasing the temperature but to extend the reaction times in order to prevent undesired opening of the lactone ring in the above-mentioned sense.

The mixture is worked up in the customary manner; the lactones can be purified by recrystallization.

The formula (IX) provides a definition of the compounds obtained in process 13. In this formula, X preferably represents hydrogen, fluorine, chlorine, bromine, methyl, ethyl, phenyloxy, methoxy, ethoxy or methylmercapto, Y preferably represents hydrogen, chlorine, methyl or methoxy, or X and Y represent methylenedioxy or ethylenedioxy, and Z preferably represents O, S or —CH=CH—.

Very particularly preferably, X represents hydrogen, fluorine, chlorine, bromine, methyl or methoxy, Y represents hydrogen, or X and Y represent methylenedioxy, and Z represents —CH=CH—.

The following compounds of the formula (IX) may be mentioned as examples: 3,3-dimethyl-4-phenacyl-γ-butyrolactone, 3,3-dimethyl-4-(4'-fluoro-phenacyl)-γ-butyrolactone, 3,3-dimethyl-4-(4'-chloro-phenacyl)-γ-butyrolactone, 3,3-dimethyl-4-(4'-bromo-phenacyl)-γ-butyrolactone, 3,3-dimethyl-4-(4'-methyl-phenacyl)-γ-butyrolactone, 3,3-dimethyl-4-(4'-methoxy-phenacyl)-γ-butyrolactone, 3,3-dimethyl-4-(4'-methylmercapto-phenacyl)-γ-butyrolactone, 3,3-dimethyl-4-(3',4'-methylenedioxy-phenacyl)-γ-butyrolactone and 3,3-dimethyl-4-(3',4'-dimethoxy)-γ-butyrolactone.

Process 15 can be represented by the following equation:

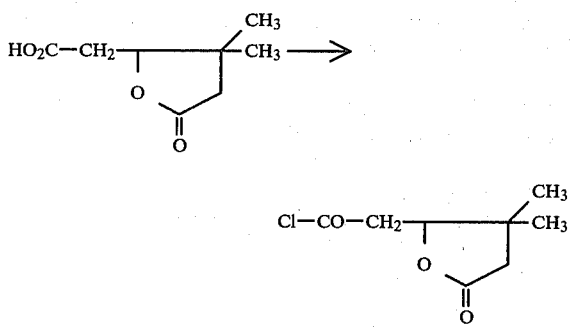

The acid of the formula (XII) used as the starting substance is known (J. Org. Chem., Volume 38, page 4,148 and J. Chem. Soc. 79, 763), but the acid chloride of the formula (XI) has not before been described in the literature. It is surprising that conversion of the acid into the acid chloride proceeds smoothly, since ring opening of the lactone usually also takes place under these conditions.

Process 15 is carried out under the conditions which are customary for the preparation of an acid chloride from an acid. Preferred chlorinating agents are thionyl chloride and phosgene. However, care must be taken that reaction times which are as short as possible are applied, in order to avoid a side reaction of the above-mentioned type. The mixture is worked up in the customary manner. The acid chloride can be purified by distillation or can be employed in process 13 in the crude form.

The active compounds obtainable by process variants 1(a), (b) and (c)—especially those containing a radical of an alcohol customary in pyrethroids—are well tolerated by plants, have a favorable level of toxicity to warm-blooded animals, and can be used for combating arthropod pests, especially insects and acarids which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus*, *Armadillidium vulgare* and *Porcellio scaber*;

from the class of the Diplopoda, for example *Blaniulus guttulatus*;

from the class of the Chilopoda, for example *Geophilus carpophagus* and *Scutigera* spec.;

from the class of the Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis*, *Periplaneta americana*, *Leucophaea maderae*, *Blattella germanica*, *Acheta domesticus*, *Gryllotalpa* ssp., *Locusta migratoria migratorioides*, *Melanoplus differentiallis* and *Schistocerca gregaria*;

from the order of the Dermaptera, for example *Forficula auricularia*;

from the order of the Isoptera, for example *Reticulitermes* ssp.;

from the order of the Anoplura, for example *Phylloxera vastatrix*, *Pemphigus* spp., *Pediculus humanus corporis*, *Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci*;

from the order of the Heteroptera, for example *Eurygaster* spp., *Dysdercus intermedius*, *Piesma quatrata*, *Cimex lectularius*, *Rhodnius prolixus* and *Triatoma* spp.;

from the order of the Homoptera, for example *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, *Myzus* spp.; *Phorodon humuli*, *Rhopalosiphum padi*, *Empoasca* spp.; *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.;

from the order of the Lepidoptera, for example *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, *Lymantra* spp., *Bucculatrix thurberiella*, *Phyllocnistis citrella*, *Agrotis* spp., *Euxoa* spp., *Feltia* spp., *Earias insulana*, *Heliothis* spp., *Laphygma exigua*, *Mamestra brassicae*, *Panolis flammea*, *Prodenia litura*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Cacoecia podana*, *Capua reticulana*, *Choristoneura fumiferana*, *Clysia ambiguella*, *Homona magnanima* and *Tortrix viridana*;

from the order of the Coleoptera, for example *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis* and *Costelytra zealandica*;

from the order of the Hymenoptera, for example *Diprion* spp., *Hoplocampa* spp., *Lasius* spp., *Monomorium pharaonis* and *Vespa* spp.;

from the order of the Diptera, for example Aedes spp., anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes Spp., Psoroptes spp., Chorioptes spp., Sacroptes spp., Tarsonemus spp., *Bryobia praetiosa*, Panonychus spp. and Tetranychus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic carbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

Process variant 1(a))

A solution of sodium ethylate (prepared from 2.5 g of sodium and 100 ml of ethanol) was added dropwise to a solution of 35 g (0.1 mol) of 6-(4'-chloro-phenyl)-4,6-dichloro-3,3-dimethyl-hex-5-enoic acid ethyl ester in 100 ml of ethanol at room temperature. The mixture was subsequently stirred for 4 hours, diluted with ice-water and rendered neutral. After extraction with methylene chloride, the organic phase was dried and concentrated on a rotary evaporator. Distillation under a high vacuum gave 26.5 g of a pale yellowish oil with a boiling point of 152°–158° C./0.08 mbar. It contained all the 4 possible stereoisomers of 2,2-dimethyl-3-[2'-chloro-2'-(4'-chlorophenyl)]-vinyl-cyclopropane-1-carboxylic acid ethyl ester. The isomer distribution was (according to the gas chromatogram): 66%:13.5%:8%:9%. The vinyl proton of the principal isomer exhibited (in $CDCl_3$) a doublet at $\delta = 5.7$ and 5.85 ppm. Mass spectrum: m/e=312.

Example 2

(Process variant 1(b))

A solution of 40 g of 6-(4'-chloro-phenyl)-4,6,6-trichloro-3,3-dimethyl-hexanoic acid ethyl ester (crude; from Example 8) in 100 ml of ethanol was added dropwise to a solution of 4.75 g of sodium in 250 ml of ethanol at room temperature. The mixture was subsequently stirred at room temperature for 2 hours and then heated to 50° C. for a further 1 hour. Ice-water was then added and the mixture was neutralized with 10% strength hydrochloric acid. After extracting the mixture twice with methylene chloride, the organic phases were dried and concentrated on a rotary evaporator and the residue was distilled under a high vacuum. 25 g of 2,2-dimethyl-3-[2'-chloro-2'-(4'-chlorophenyl)]-vinyl-cyclopropane-1-carboxylic acid ethyl ester of boiling point 154°–162° C./0.1 mbar were obtained.

Example 3

(Process variant 1(c))

A solution of 40 g of sodium in 700 ml of ethanol was added to a solution of 32.7 g of 6-(4'-chloro-phenyl)-4,6,6-trichloro-3,3-dimethyl-hexanoic acid chloride (crude, still contained $POCl_3$; from process 8) in 500 ml of toluene, while cooling with ice. The mixture was stirred at room temperature for 8 hours and then heated to 50° C. for a further 1 hour, ice-water was added, the mixture was neutralized with 10% strength hydrochloric acid, the toluene phase was separated off and the aqueous phase was extracted with methylene chloride. The combined organic phases were dried and the solvents and the phosphoric acid triethyl ester formed were distilled off. The residue was purified by distillation under a high vacuum. 19.6 g of 2,2-dimethyl-3-[2'-chloro-2'-(4'-chloro-phenyl)]-vinyl-cyclopropane-1-carboxylic acid ethyl ester were obtained.

Example 4

(Process variant 1(c))

2,2-Dimethyl-3-[2'-chloro-2'-phenyl]vinyl-cyclopropane-1-carboxylic acid ethyl ester was obtained from 6-phenyl-4,6,6-trichloro-3,3-dimethyl-hexanoic acid chloride and sodium ethylate analogously to Example 3.

Example 5

(Process variant 1(a))

A solution of 6.3 g of 6-(4'-chloro-phenyl)-4-chloro-3,3-dimethyl-hex-5-enoic acid ethyl ester in 30 ml of ethanol was added dropwise to a solution of sodium ethylate (prepared from 0.7 g of sodium and 30 ml of ethanol) at room temperature. The mixture was subsequently stirred for 4 hours, diluted with ice-water and rendered neutral. After extraction with methylene chloride, the organic phase was dried and concentrated in a rotary evaporator and the residue was subjected to incipient distillation under a high vacuum at 60° C. 4.6 g of 2,2-dimethyl-3-[2'-(4'-chloro-phenyl)-vinyl]-cyclopropane-1-carboxylic acid ethyl ester (isomer mixture) were obtained.

Example 6

(Process 6(a))

A solution of 6-(4'-chloro-phenyl)-4,6,6-trichloro-3,3-dimethyl-hexanoic acid methyl ester was warmed to about 40° C. in toluene for 1 hour. After distilling off the toluene in vacuo, 6-(4'-chloro-phenyl)-4,6-dichloro-3,3-dimethyl-hex-5-enoic acid methyl ester remained. The structure was proved by the NMR spectrum (olefinic proton at 6.2 ppm in $CDCl_3$).

Example 7

(Process 6(b))

20 Times the equimolar amount of dry methanol was added to a solution of 6-(4'-chloro-phenyl)-4,6,6-trichloro-3,3-dimethyl-hexanoic acid chloride (crude; still contained $POCl_3$; from process 8) in toluene at 20° C. and the mixture was then warmed to 40° C. for a further 1 hour. After subsequently stirring the mixture for 4 hours (without heating), the solvents and phosphoric acid ester were removed in vacuo. The residue was identical to the product obtained in Example 6.

Example 8

(Process 6(c))

40 g of phosphorus pentachloride were added to a solution of 23.2 g of 3,3-dimethyl-4-(4'-chloro-phenacyl)-γ-butyrolactone in 400 ml of toluene and the mixture was stirred at room temperature until all the $PCl_5$ had dissolved. 120 ml of ethanol were then added dropwise at 20° C., the mixture was subsequently warmed to 45° C. for 1 hour and stirring was then continued until the mixture had reached room temperature again. It was then poured into a large quantity of ice-water and rendered neutral. The toluene phase was separated off, dried and concentrated on a rotary evaporator. After distilling off the solvents and the phosphoric acid triethyl ester, 24 g of a dark oil, which consisted mainly of 6-(4'-chloro-phenyl)-4,6-dichloro-3,3-dimethyl-hex-5-enoic acid ethyl ester and could be further processed according to process variant 1(a) (see Example 1), remained.

Example 9

(Process 6(d))

(a) 26.6 g (0.1 mol) of the lactone from Example 15 were reduced in 100 ml of absolute ethanol with 1.13 g (30 mmol) of sodium borohydride at room temperature. After working up the mixture with methylene chloride and dilute hydrochloric acid, 28 g (100%) of 4,4- dimethyl-dihydro-5-[2-(4-chlorophenyl)-2-hydroxy-ethyl]-2-(3H)-furanone were obtained as an oil.

(b) 28 g (0.1 mol) of the hydroxylactone from Example 9(a) were reacted with 11.2 g (0.11 mol) of acetic anhydride and a trace of p-toluenesulphonic acid in the course of 2 hours, while heating, to give the acetoxy derivative, which distilled at a boiling point of 198° C. to 202° C./0.3 mm Hg; 20.5 g (72%) of the acetoxylactone.

(c) Pyrolysis of 14.6 g of the acetoxy compound from Example 9(b) in a toluene solution of 400° C. over glass rings in a stream of $N_2$ led to 9.6 g (80%) of the p-chlorostyryllactone of melting point 64° C.-66° C. (boiling point: 155°-158° C./0.1 mm Hg).

NMR (CDCl$_3$): δ1.05 (s, 3H), 1.2 (s, 3H), 2.45 (s, 2H); 4.7 (d, J=6 Hz, 1H); 6.1 (dd, J=6 and 15 Hz, 1H); and 6.7 (d, J=15 Hz, 1H).

From the hydroxylactone obtained in Example 9(a), the p-chlorostyryllactone could be obtained directly in a distillation, using an oil pump, in the presence of oxalic acid.

(d) 8 g of 3,3-dimethyl-4-[2'-(4'-chloro-phenyl)-vinyl]; γ-butyrolactone were dissolved in 50 ml of ethanol and dry hydrogen chloride was passed in until the exothermic reaction had subsided. After distilling off the solvent, 8.8 g of crude 6-(4'-chloro-phenyl)-4-chloro-3,3-dimethyl-hex-5-enoic acid ethyl ester, which was employed directly in process variant 1(a) (see Example 5), remained.

1H-NMR (CDCl$_3$): δ(ppm)=1.0-1.3 (m, 9H); 2.15-2.65 (g, 2H); 3.9-4.3 (g, 2H); 4.6-4.8 (d, 1H); 5.98-6.78 (m, 2H); and 7.1-7.45 (m, 4H).

Example 10

(Process 7)

9.6 g of 6-(4'-chloro-phenyl)-6-oxo-4-chloro-3,3-dimethyl-hexanoic acid ethyl ester were dissolved in 50 ml of toluene, and 6.7 g of phosphorus pentachloride were added at room temperature. The mixture was subsequently stirred at room temperature for 9 hours, poured onto 100 ml of ice-water and rendered neutral and the toluene phase was separated off. After drying the toluene phase and distilling off the toluene at room temperature, 8 g of an oil which, according to the NMR spectrum, consisted of 6-(4'-chloro-phenyl)-4,6,6-trichloro-3,3-dimethyl-hexanoic acid ethyl ester remained. The oil could be further reacted according to process variant 1(b).

NMR (CDCl$_3$): δ1.0-1.3 (m, 9H); 2.4 (m, 2H); 2.9-3.5 (m, 2H); 3.9-4.2 (m, 2H); 4.6-4.8 (dd, 1H); and 7.3-8.0 (m, 4H);

Example 11

(Process 8)

26.7 g of 3,3-dimethyl-4-(4'-chloro-phenacyl)-γ-butyrolactone were dissolved in 500 ml of toluene, and 46 g of phosphorus pentachloride were added. The mixture was subsequently stirred at room temperature for 18 hours and phosphorus oxychloride and toluene were then distilled off at room temperature in vacuo. 38 g of a brown oil, which was identified as 6-(4'-chlorophenyl)-4,6,6-trichloro-3,3-dimethyl-hexanecarboxylic acid chloride by the IR and NMR spectra, remained.

Example 12

(Process 11)

80.1 g of 3,3-dimethyl-4-(4'-chloro-phenacyl)-γ-butyrolactone were dissolved in 500 ml of ethanol, and dry hydrogen chloride was passed in until the temperature had reached 50° C. A slow stream of hydrogen chloride was then passed through the solution at 50° C., initially with cooling, for 3 hours, and the introduction was then continued until the mixture had reached room temperature again. Distilling off the ethanol in vacuo gave 100 g of 6-(4'-chloro-phenyl)-6-oxo-4-chloro-3,3-dimethyl-hexanoic acid ethyl ester of refractive index $n_D^{20}=1.528$.

1H-NMR (CDCl$_3$): δ=1.05-1.4 ppm (9H, m), 2.42 ppm (2 H); 3.25-3.55 ppm (2 H); 3.95-4.4 ppm (2 H); 4.6-4.85 (1 H); and 7.3-8.05 ppm (m, 4H).

Example 13

(Process 11)

134 g of 3,3-dimethyl-4-(4'-chloro-phenacyl)-γ-butyrolactone were dissolved in 215 g of thionyl chloride in a 0.7 liter enamel autoclave. 100 g of ethanol were then pumped in and the mixture was kept at 50° C. for 4 hours. After cooling and letting down, excess thionyl chloride and sulphurous acid ethyl ester were distilled off. The residue essentially consisted of 6-(4'-chloro-phenyl)-6-oxo-4-chloro-3,3-dimethyl-hexanoic acid ethyl ester.

Example 14

(Process 11)

134 g of 3,3-dimethyl-4-(4'-chloro-phenacyl)-γ-butyrolactone were dissolved in 215 g of thionyl chloride in a 0.7 liter autoclave with a glass liner. 100 g of methanol were then pumped in and the mixture was heated to 50° C. for 4 hours. After working up as in Example 10, 6-(4'-chloro-phenyl)-6-oxo-4-chloro-3,3-dimethyl-hexanoic acid methyl ester was obtained.

Example 15

(Process 12)

71 g (0.5 mol) of 3,3-dimethyl-4-pentenoic acid methyl ester were added dropwise to a mixture of 87.5 g (0.5 mol) of p-chlorobenzoyl chloride and 130.3 g (0.5 mol) of tin tetrachloride at 20° C., while cooling with ice. After being left to stand overnight, the reaction mixture had solidified. It was taken up in methylene chloride, the methylene chloride mixture was filtered and the filtrate was extracted by shaking with dilute hydrochloric acid. After drying and stripping off the solvent in vacuo, 111.1 g of crude product (about 83%), which crystallized completely, were obtained. Recrystallization from 120 ml of ethanol gave 3,3-dimethyl-4-(4'-chloro-phenacyl)-γ-butyrolactone of melting point 76°-80° C.

NMR (CDCl$_3$): δ1.15 (s, 3H), 1.25 (s, 3H), 2.45 (m 2H), 2.8-3.65 (81, 2H), 4.9 (dd, 1H) and 7.3-8.05 (m, 4H).

Example 16

(Process 12)

26 g (0.1 mol) of tin tetrachloride were added dropwise to a solution of 17.5 g (0.1 mol) of p-chlorobenzoyl chloride and 14.2 g (0.1 mol) of 3,3-dimethyl-4-pentenoic acid methyl ester in 100 ml of methylene chloride at 0° C. and the mixture was then heated under reflux for 8 hours until the evolution of gas had ended. After working up with dilute hydrochloric acid, 20.9 g of a lactone, which corresponded to the product obtained in Example 15, were obtained.

Example 17

(Process 12)

26 g (0.1 mol) of tin tetrachloride were added dropwise to a solution of 14.1 g (0.1 mol) of benzoyl chloride and 14.2 g (0.1 mol) of 3,3-dimethyl-4-pentenoic acid methyl ester in 100 ml of methylene chloride at room temperature and the mixture was then heated under reflux for 8 hours until the evolution of gas had ended. After acidifying with dilute hydrochloric acid, 21.6 g of 3,3-dimethyl-4-phenacyl-γ-butyrolactone of melting point 86°–88° C. were obtained.

Example 18

(Process 12)

3,3-Dimethyl-4-(4'-nitro-phenyl)-γ-butyrolactone of melting point 107°–110° C. was obtained from 4-nitrobenzoyl chloride and 3,3-dimethyl-4-pentenoic acid methyl ester analogously to Example 17.

Example 19

(Process 12)

3,3-Dimethyl-4-(4'-chloro-3'-nitro-phenyl)-γ-butyrolactone (melting point: 134°–136° C.) was obtained analogously to Example 17.

Example 20

(Process 15)

17.2 g of 3,3-dimethyl-4-carboxymethyl-γ-butyrolactone were mixed with 60 ml of thionyl chloride and the mixture was heated to 80° C. for 1 hour. The excess thionyl chloride was then distilled off under normal pressure, the last residues under a waterpump vacuum. The residue consisted of 3,3-dimethyl-4-chlorocarbonylmethyl-γ-butyrolactone and could be used directly for process 13. However, the product could also be further purified by distillation: boiling point: 130°–140° C./0.3 mbar.

Example 21

(Process 13)

80 g of aluminum chloride were initially introduced in 300 ml of methylene chloride, and 59 g of 3,3-dimethyl-4-chlorocarbonylmethyl-γ-butyrolactone, dissolved in 150 ml of methylene chloride, were added dropwise at 0°–5° C. 39.2 g of chlorobenzene, dissolved in 50 ml of methylene chloride, were then added dropwise, also at 0°–5° C. The mixture was then allowed to come to room temperature and was subsequently stirred at room temperature for a further 7 hours. After pouring the batch into ice-water, the organic phase was separated off and washed until neutral. After drying and distilling off the solvent, 76 g of crude 3,3-dimethyl-4-(4'-chlorophenacyl)-γ-butyrolactone, which was recrystallized from ethanol, were obtained. Melting point: 78°–80° C.

Examples 22 and 23

(Process 13)

The following compounds were obtained analogously to Example 21: 3,3-dimethyl-4-(4'-methylphenacyl)-γ-butyrolactone (melting point: 96° C.) and 3,3-dimethyl-4-(phenacyl)-γ-butyrolactone (melting point: 86°–88° C.).

We claim:

1. A compound of the formula

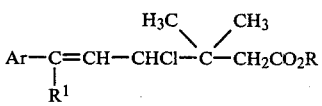

in which

Ar is a phenyl or naphthyl radical optionally substituted by at least one halogen, cyano, nitro, aryl, aralkyl, aryloxy, arylthio, $C_{1-4}$-alkyl, $C_{1-4}$-alkoxy, $C_{1-4}$-alkylthio, $C_{1-2}$-halogenoalkyl, $C_{1-4}$-halogenoalkoxy, $C_{1-4}$-alkylsulphonyl, halogen-substituted $C_{1-4}$-alkylsulphonyl or $C_{1-2}$-dialkylamino radical, R is $C_{1-4}$-alkyl or a 3-phenoxybenzyl radical which is optionally substituted by halogen or cyano, and $R^1$ is fluorine or chlorine.

2. A compound of the formula

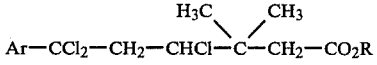

in which

Ar is a phenyl or naphthyl radical optionally substituted by at least one halogen, cyano, nitro, aryl, aralkyl, aryloxy, arylthio, $C_{1-4}$-alkyl, $C_{1-4}$-alkoxy, $C_{1-4}$-alkylthio, $C_{1-2}$-halogenoalkyl, $C_{1-4}$-halogenoalkoxy, $C_{1-4}$-alkylsulphonyl, halogen-substituted $C_{1-4}$-alkylsulphonyl or $C_{1-2}$-dialkylamino radical, R is methyl or ethyl.

3. A compound of the formula

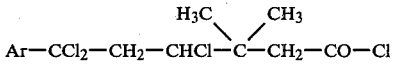

in which

Ar is a phenyl or naphthyl radical optionally substituted by at least one halogen, cyano, nitro, aryl, aralkyl, aryloxy, arylthio, $C_{1-4}$-alkyl, $C_{1-4}$-alkoxy, $C_{1-4}$-alkylthio, $C_{1-2}$-halogenoalkyl, $C_{1-4}$-halogenoalkoxy, $C_{1-4}$-alkylsulphonyl, halogen-substituted $C_{1-4}$-alkylsulphonyl or $C_{1-2}$-dialkylamino radical.

4. A compound according to claim 1, in which

Ar is phenyl or naphthyl substituted by at least one halogen, and

R is an α-cyano-3-phenoxybenzyl radical optionally substituted on the benzyl moiety by halogen.

* * * * *